(12) United States Patent
Correia et al.

(10) Patent No.: US 8,435,241 B2
(45) Date of Patent: May 7, 2013

(54) KEEL PUNCH IMPACTOR WITH CONNECTION DEVICE

(75) Inventors: Jose A. Correia, New Bedford, MA (US); John Cuneo, Norton, MA (US); Michael Fortin, Acushnet, MA (US); Jim Kennedy, Berkley, MA (US); Carl Livorsi, Lakeville, MA (US); Troy Martin, Pierceton, IN (US); John J. McMorrow, Franklin, MA (US); Rebecca Zimmerman, Spotsylvania, VA (US)

(73) Assignee: DePuy Products, Inc., Warsaw, IN (US)

( * ) Notice: Subject to any disclaimer, the term of this patent is extended or adjusted under 35 U.S.C. 154(b) by 879 days.

(21) Appl. No.: 12/340,012

(22) Filed: Dec. 19, 2008

(65) Prior Publication Data
US 2010/0076438 A1 Mar. 25, 2010

Related U.S. Application Data

(60) Provisional application No. 61/008,375, filed on Dec. 20, 2007.

(51) Int. Cl.
*A61B 17/00* (2006.01)
*A61F 2/46* (2006.01)

(52) U.S. Cl.
USPC .............................. 606/79; 606/86 R; 606/85

(58) Field of Classification Search .................... 606/79, 606/86, 53, 99–100, 102, 104, 85
See application file for complete search history.

(56) References Cited

U.S. PATENT DOCUMENTS

| D269,547 S | 6/1983 | Rosenthal |
| D338,270 S | 8/1993 | Stephens et al. |
| 5,356,414 A | 10/1994 | Cohen et al. |
| 5,690,636 A | 11/1997 | Wildgoose et al. |
| 5,702,464 A | 12/1997 | Lackey et al. |
| 5,976,147 A | 11/1999 | LaSalle et al. |
| 5,989,261 A | 11/1999 | Walker et al. |
| 6,159,216 A | 12/2000 | Burkinshaw et al. |

(Continued)

FOREIGN PATENT DOCUMENTS

| EP | 1415625 A2 | 5/2004 |
| WO | 9925263 A1 | 5/1999 |
| WO | 0013597 A1 | 3/2000 |

OTHER PUBLICATIONS

European Search Report in corresponding European patent application EP12174174.8, dated Sep. 6, 2012 (7 pages).

(Continued)

*Primary Examiner* — Bruce E Snow
(74) *Attorney, Agent, or Firm* — Maginot, Moore & Beck, LLP

(57) ABSTRACT

A keel punch impactor comprises a main body having an interior bore. A locking shaft is positioned in the interior bore of the main body, the locking shaft defining a shaft axis. An actuator is in contact with the locking shaft. The actuator is moveable between a first position and a second position. The position of the locking shaft is moved within the interior bore of the main body upon movement of the actuator. In particular, the locking shaft is moved such that the shaft axis is offset when the actuator is moved from the first position to the second position. When the shaft is moved, a head on the shaft is moved into or out of alignment with a boss extending from the main body of the keel punch impactor.

18 Claims, 3 Drawing Sheets

U.S. PATENT DOCUMENTS

| | | | |
|---|---|---|---|
| 6,344,043 | B1 | 2/2002 | Pappas |
| 6,355,045 | B1 | 3/2002 | Gundlapalli et al. |
| 6,821,470 | B2 | 11/2004 | Gundlapalli et al. |
| D518,178 | S | 3/2006 | Christiansen |
| 7,291,174 | B2 | 11/2007 | German et al. |
| 7,695,519 | B2 | 4/2010 | Collazo |
| D619,251 | S | 7/2010 | Justiniano-Garcia et al. |
| 2005/0075640 | A1 | 4/2005 | Collazo et al. |
| 2006/0089641 | A1 | 4/2006 | Collazo |
| 2008/0221569 | A1 | 9/2008 | Moore et al. |
| 2010/0016979 | A1 | 1/2010 | Wyss et al. |
| 2010/0076438 | A1 | 3/2010 | Correia et al. |
| 2011/0178605 | A1 | 7/2011 | Auger et al. |

OTHER PUBLICATIONS

P.F.C. Sigma Rotating Platform Knee System with M.B.T. Tray, Primary Procedure with a Curved or Posterior Stablised Implant, DePuy, 2003 (43 pages).

Zimmer NexGen LCCK, Surgical Technique for use with LCCK 4-in-1 Instrumentation, Zimmer, 2009 (52 pages).

Vanguard SSK Revision System, Surgical Technique, Biomet, 2008 (64 pages).

Coordinate Ultra Revision Knee System, Surgical Technique, Depuy, 1997 (24 pages).

LCS Complete Knee Revision, Surgical Technique, DePuy, 2011 (60 pages).

P.F.C. Sigma Knee System, Revision, Surgical Technique, DePuy, 2000 (66 pages).

Sigma Revision and M.B.T. Revision Tray, Surgical Technique, DePuy, 2012 (84 pages).

S-Rom Noiles Rotating Hinge, Surgical Technique, DePuy, 2012 (76 pages).

GMK Revision, Surgical Technique, Ref 99.27.12 US rev.1, Medacta International, published at least as early as Dec. 19, 2007 (52 pages).

Legion Revision Knee System, Surgical Technique, Smith & Nephew, 2005 (40 pages).

Sigma High Performance Instruments, Product Rationale, DePuy, 2007 (12 pages).

Sigma High Performance Instruments, Classic Surgical Technique, DePuy, 2010 (52 pages).

LCS High Performance Instruments, Surgical Technique, DePuy, 2008 (44 pages).

KEEL PUNCH IMPACTOR WITH CONNECTION DEVICE

This application claims the benefit of U.S. Provisional Application Ser. No. 61/008,375, filed Dec. 20, 2007, the disclosure of which is herein incorporated by reference.

FIELD

This invention relates to the field of surgical instruments, and more particularly to a device for connecting surgical instruments used during orthopedic surgery.

BACKGROUND

Surgical procedures often involve the use of various mechanical devices that assist the surgeon in performing various tasks during the surgical procedure. Many of these surgical devices are multi-part devices that require connection (or disconnection) during the procedure. It is desirable to make the connection or disconnection of these devices as easy as possible to assist the surgeon during the surgical procedure. Of course, during surgical procedures the surgical devices are often surrounded by patient tissue or other surgical devices, leaving limited options for connection and disconnection arrangements.

One example of a multi-part surgical device is the keel punch used during orthopedic knee surgery. In general, the keel punch includes an impactor that is connected to a broach prior to or during surgical procedure. During a total knee replacement procedure, the impactor of the keel punch is used to drive the broach into the patient's tibia. The impactor must then be removed from the broach, leaving the broach embedded in the tibia.

In view of the foregoing, it would be desirable to provide an orthopedic surgical device that facilitates quick and easy connection or disconnection between two components of the surgical device. In particular, it would be advantageous to provide a keel punch impactor with a handle that could be quickly and easily attached to and/or removed from the broach of the impactor during the surgical procedure. It would also be advantageous if the handle could be easily connected to the broach with minimal interference from patient tissue and/or other surgical devices during the surgical procedure.

SUMMARY

Disclosed herein is a surgical instrument connection device. In at least one embodiment, the device comprises a main body having an interior bore. A locking shaft is positioned in the interior bore of the main body, the locking shaft defining a shaft axis. An actuator is in contact with the locking shaft. The actuator is moveable between a first position and a second position. The position of the locking shaft is moved within the interior bore of the main body upon movement of the actuator. In particular, the locking shaft is moved such that the shaft axis is offset when the actuator is moved from the first position to the second position.

In at least one embodiment the surgical connection device includes a boss extending from the main body and a lip or flange positioned on the end of the locking shaft. The flange is flush with the boss or contained within the footprint of the boss when the actuator is in the second position. The flange is offset from the boss or protrudes outside of the boss when the actuator is in the first position. A broach is connected to the main body by moving the actuator from the first position to the second position such that the lip is flush with the boss. The mouth of the broach is then engaged with the boss. When the actuator is returned to the first position, the lip of the locking device engages a shoulder on the broach to lock the broach to the main body. In at least one embodiment, the actuator includes a button positioned in a transverse passage provided in the main body. The transverse passage extends between an outer surface of the main body and the interior bore.

In at least one embodiment, the surgical instrument connection device is provided on a keel punch impactor. The keel punch impactor comprises a handle portion including an impact surface and a coupling portion connected to the handle portion. The coupling portion defines an elongated interior cavity configured to receive an elongated member. The actuator is in contact with the elongated member in the interior cavity. The actuator is moveable between a first position and a second position, wherein the position of the elongated member is shifted laterally within the elongated interior cavity when the actuator is moved from the first position to the second position.

In at least one embodiment, the keel punch impactor comprises a handle portion defining an impact axis. A coupling portion is connected to the handle portion, the coupling portion including an end portion with a footprint provided along the impact axis. A flange is provided at the end portion of the coupling portion. The flange is moveable between a first position and a second position. When in the second position, the flange is substantially contained within the footprint of the end portion. When in the first position, the flange protrudes outside the footprint of the end portion.

The above described embodiments, features and advantages, as well as others, will become more readily apparent to those of ordinary skill in the art by reference to the following detailed description and accompanying drawings.

DESCRIPTION

Figure 1:
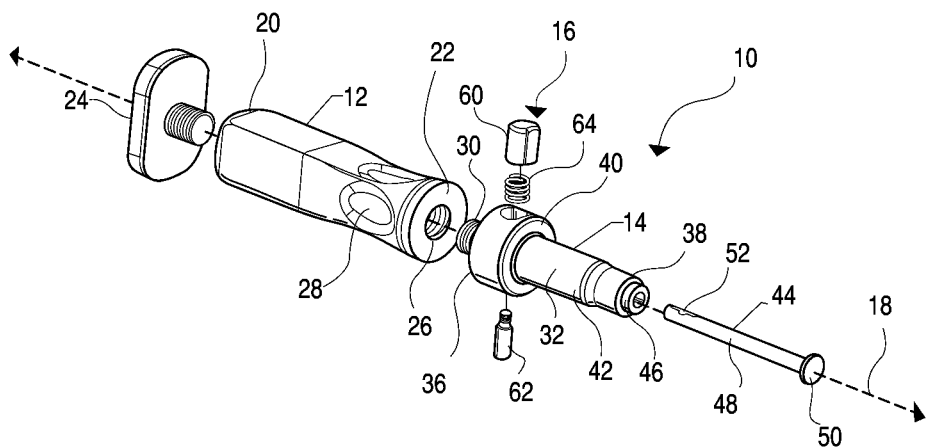
FIG. 1 shows an exploded isometric view of a keel punch impactor.
Figure 2:
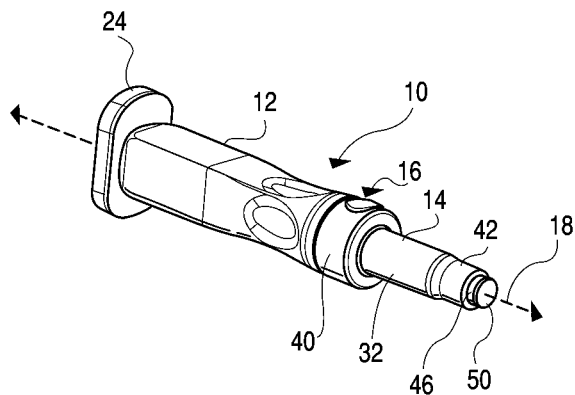
FIG. 2 shows a perspective view of the assembled keel punch impactor of FIG. 1.

With reference to FIGS. 1 and 2, a surgical instrument connection device is shown as part of an orthopedic keel punch impactor 10. The keel punch impactor 10 generally includes a handle portion 12 connected to a coupling portion 14. An actuator 16 is provided on the coupling portion 14 of the instrument. The keel punch impactor 10 is comprised of a relatively rigid biocompatible material, such as stainless steel. However, it will be recognized that various other materials may be used to form the keel punch impactor 10.

The handle portion 12 includes a proximal end 20 and a distal end 22. An impact plate 24 is threadedly connected to the handle 12 at the proximal end 20. The impact plate 24 includes a flat outer surface that is designed to be struck by a hammer or other tapping device in order to force the keel punch impactor 10 in the axial direction (i.e., along impact axis 18).

The central portion of the handle 12 is designed and dimensioned to be grasped by the hand of a surgeon or other surgical team member. The handle 12 may include various contours and other features, such as finger indentations 28 to assist the user in grasping the handle.

A threaded bore 26 is formed in the distal end 22 of the handle 12. The threaded bore 26 is configured to receive a threaded post 30 on the coupling portion 14. Engagement of the post 30 with the bore 26 and subsequent rotation of the handle 12 relative to the coupling portion 14 allows the handle 12 to be secured to the coupling portion 14.

The coupling portion 14 generally comprises a main body 32 that is connected to the handle 12. The post 30 of the coupling portion 14 is provided on the proximal end 36 of the main body. As set forth above, the threaded post 30 facilitates threaded engagement of the coupling portion 14 with the handle portion 12.

An enlarged collar portion 40 is provided on the main body 32. The collar portion 40 is adjacent to an elongated neck portion 42 on the main body. The neck portion 42 extends between the collar portion 40 and a boss 46. The boss 46 extends from the distal end 38 of the main body 32. The shape of the outer surface of the boss 46 defines a footprint for the boss 46. In the embodiment shown herein, the footprint is a circular footprint, however, it will be recognized that the footprint of the boss may take on various other shapes in different embodiments. As will be explained in further detail below, the boss 46 is configured to engage a broach member that fits over the boss.

Figure 3:
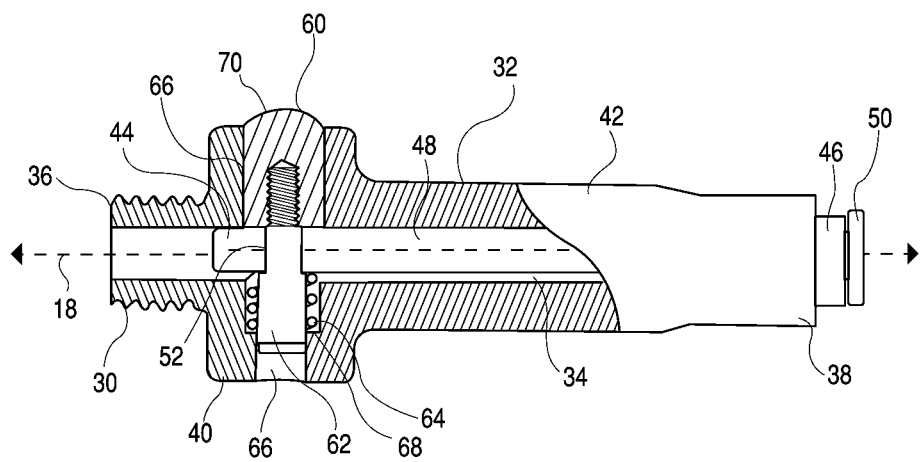
FIG. 3 shows a cutaway side view of the coupling portion of the keel punch impactor of FIG. 1 with the shaft in a locking position.

With reference now to FIG. 3, the main body 32 of the coupling portion 14 includes an interior bore 34 that extends from the proximal end 36 to the distal end 38 of the main body 32. An elongated member in the form of a locking shaft 44 is positioned in the interior bore 34 of the main body, with the locking shaft 44 extending substantially parallel to the axis 18. One end of the locking shaft 44 extends through the boss 46 and protrudes outward from the distal end 38 of the main body 32. An opposite end of the locking shaft 44 engages the actuator 60 provided in the collar portion 40 of the main body 32.

Figure 4:
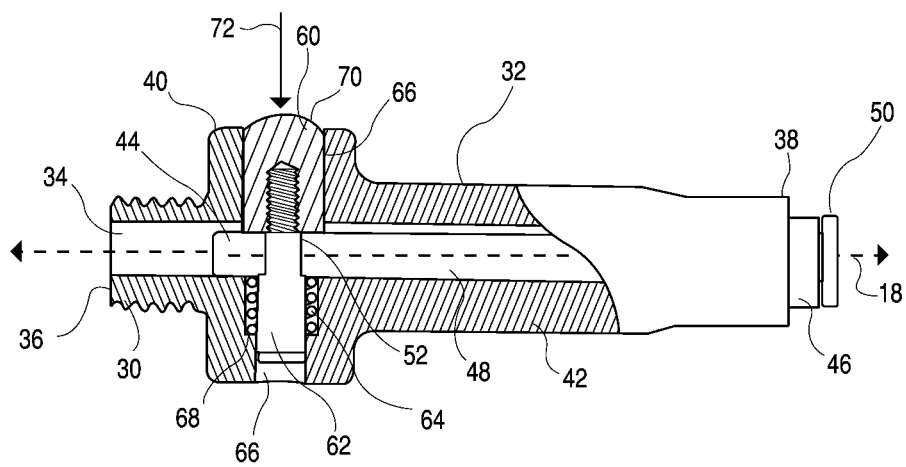
FIG. 4 shows the coupling portion of FIG. 3 with the shaft in an unlocking position.

As can be seen in FIGS. 3 and 4, the diameter of the interior bore 34 of the coupling portion 14 is substantially larger than the diameter of the locking shaft 44. Accordingly, the locking shaft 44 is moveable laterally within the interior bore 34 (i.e., in a direction substantially perpendicular to the axis 18) between a first position and a second position. The first position of the locking shaft 44 is shown in FIG. 3 with the locking shaft 44 closer to a first side of the interior bore 34 (in the orientation shown, the locking shaft 44 is closer to the upper side of the interior bore 34). The second position of the locking shaft is shown in FIG. 4 with the locking shaft 44 closer to an opposite side of the interior bore 34 (in the orientation shown, the locking shaft 44 is closer to the lower side of the interior bore 34). In both the first position and the second position, the axis of the locking shaft remains substantially parallel to the impact axis 18.

The locking shaft 44 includes an elongated trunk portion 48 connected to a head portion 50. The head portion 50 provides an enlarged portion or lateral protrusion at the distal end of the locking shaft 44. In at least one embodiment, the head portion 50 has the same general shape as the boss 46. When the head portion 50 is aligned with the boss 46 (as shown in FIG. 4), the outline of the head portion 50 substantially matches the footprint of the boss 46 or is contained within the footprint of the boss. When the head portion 50 is not aligned with the boss (as shown in FIG. 3), the head provides a lip or flange that protrudes outside of the footprint of the boss. A hole 52 is provided on the end of the locking shaft 44 opposite the head portion 50 to facilitate engagement of the locking shaft with the actuator 16.

The actuator 16 is in contact with the locking shaft and is operable to move the locking shaft laterally within the internal bore 34 between two positions, such as the position shown in FIG. 3 and the position shown in FIG. 4. The actuator includes a pushbutton 60, a bolt 62, and a spring 64. The bolt 62 passes through the hole 52 provided in the proximal end of the locking shaft 44. The bolt is connected to the button 60 on one side of the locking shaft 44 and passes through the center of the spring 64 on the opposite side of the locking shaft.

The actuator 16 is positioned in a seat in the collar portion 40 of the main body. The seat is provided as a transverse passage 66 that extends completely through the coupling portion 14, the transverse passage 66 being substantially perpendicular to the impact axis 18. The pushbutton 60 is provided as a cylindrical member on one side of the seat. One end of the pushbutton 60 abuts the locking shaft 44 in the interior bore 34 of the main body 32. This end of the pushbutton 60 also includes a threaded cavity that receives a threaded portion of the bolt 62. The opposite end of the pushbutton includes an exposed surface/end 70 that protrudes outward from the collar portion 40 of the main body 32.

The spring 64 is positioned on the opposite side of the transverse passage 66 from the pushbutton 60. The spring 64 is trapped between a shoulder 68 in the transverse passage 66 and the locking shaft 44. The bolt 62 extends through the spring 64 and the locking shaft 44 and connects to the pushbutton 60 on the opposite side of the locking shaft from the spring.

In operation, the actuator is configured to move between a first position and a second position. The first position is shown in FIG. 3. In this position, no force is being applied to the exposed end 70 of the pushbutton 60. Accordingly, the spring 64 acts against the shoulder 68 and force the locking shaft 44 to the upper side of the interior bore 34. With the locking shaft 44 in this position, the exposed end 70 of the pushbutton 60 is forced its outermost position away from the main body of the coupling member 14. Also, when the locking shaft 44 is in this position, the head 50 is misaligned with the boss 46, with a lip on the head 50 provided outside of the footprint of the boss 46, as shown in FIG. 3.

The second position of the actuator is shown in FIG. 4. In this position, a user is applying a force to the pushbutton 60 in the direction of arrow 72. The force applied by the user forces the pushbutton 60 further into the transverse passage 66. As the pushbutton 60 is forced further into the transverse passage 66, the pushbutton 60 forces the locking shaft 44 against the opposite side of the interior bore 34 (i.e., the lower side of the interior bore in the orientation of FIG. 4). This also causes the spring to be compressed in the transverse passage between the locking shaft 44 and the shoulder 68. With the locking shaft 44 in this position in the interior bore 34, the head 50 of the locking shaft 44 is aligned with the footprint of the boss 46, as shown in FIG. 4.

When the user removes the force against the pushbutton 60, the compressed spring 64 once again acts against the locking shaft 44, forcing it toward the opposite side of the interior bore (i.e., the upper side of the interior bore as shown in FIG. 3). This action also causes the head 50 of the locking shaft 44 to be misaligned with the boss 46 and forces the pushbutton 60 further out of the transverse passage 66. Accordingly, although the actuator is moveable between a first position (e.g., FIG. 3) and a second position (e.g., FIG. 4), it is biased toward the first position.

Figure 5:
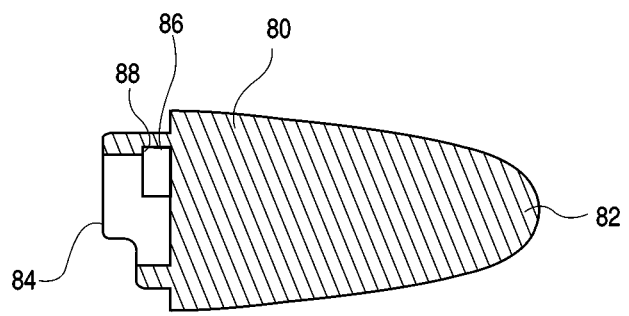
FIG. 5 shows a cross-sectional view of a broach for connection to the coupling portion of FIG. 4.

With reference now to FIG. 5, a broach 80 is shown configured for connection to the coupling portion 14 of the keel punch impactor 10. The broach 80 is generally a pointed instrument configured to be driven into the bone, such as a keel configured to be driven into the medullary canal of the tibia. It will be recognized that the broach 80 of FIG. 5 is merely exemplary and broaches of various configurations, sizes and shapes may be used with the keel punch impactor 10 disclosed herein.

The broach 80 of FIG. 5 includes a distal tip 82 on one end and a mouth 84 on the opposite end. The mouth 84 of the broach 80 is designed to fit over the boss 46 protruding from the main body 32 of the coupling portion 14. An interior groove 86 is formed within the mouth 84. The groove is defined by an interior shoulder 88 configured to engage the edge of the head 50.

Figure 6:
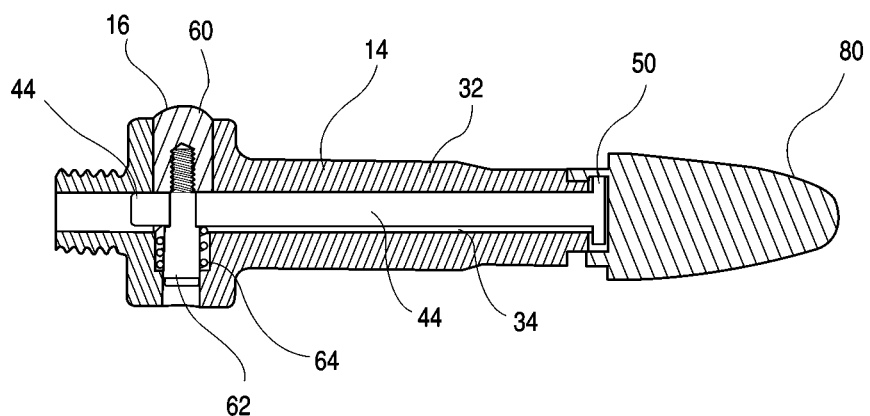
FIG. 6 shows the broach of FIG. 5 connected to the coupling portion of FIG. 3.

In order to connect the broach 80 to the impactor 10, the user first presses the pushbutton 60, forcing the locking shaft 44 against one side of the interior bore 34, as shown in FIG. 4. In this position, the head 50 of the locking shaft 44 is aligned with the boss 46. Next, the head 50 and boss 46 are inserted into the mouth 84 of the broach 80 along the impact axis 18. The user then releases the pushbutton 80, causing the spring to force the locking shaft 44 to the opposite side of the interior bore 34, as shown in FIG. 3. When the locking shaft moves to the opposite side of the interior bore, the head 50 on the locking shaft 44 becomes misaligned with the boss 46, and the edge of the head 50 moves into the groove 86 on the broach. When the edge of the head 50 moves into the groove 86, the head 50 abuts the shoulder 88 on the broach, as shown in FIG. 6. With this relationship, the broach 80 is locked in place on the coupling portion 14 in the direction of axis 18.

To release the broach 80 from the coupling portion 14, the user simply presses the pushbutton 60 inward, thus causing the head 50 to be removed from the shoulder 88 of the broach 80 and aligned with the boss 46 on the coupling portion 14. The broach 80 may then be removed from the coupling portion 14 by removing the mouth 84 of the broach 80 from the boss 44 in the direction of impact axis 18.

Although the present invention has been described with respect to certain preferred embodiments, it will be appreciated by those of skill in the art that other implementations and adaptations are possible. For example, although the structure of the actuator has been described as a bolt passing sequentially through the spring, the locking shaft, and into the pushbutton, the actuator could also be configured such that the bolt passes sequentially through the pushbutton and the spring and then passes into the locking shaft. This is but one example of an alternative embodiment, and it will be recognized that the elements described herein may take on different shapes and forms than those described herein. Those of skill in the art will also recognize that various components and features described herein, including the handle portion, the coupling portion, the actuator, the broach, or any other component, could be implemented differently than that described herein. Moreover, there are advantages to individual advancements described herein that may be obtained without incorporating other aspects described above. Therefore, the spirit and scope of the appended claims should not be limited to the description of the preferred embodiments contained herein.

What is claimed is:

1. An orthopedic keel punch impactor comprising:
   a first orthopedic keel punch impactor portion including an impact surface;
   a second orthopedic keel punch impactor portion connected to the first orthopedic keel punch impactor portion, the second orthopedic keel punch impactor portion defining an elongated interior cavity defining a longitudinal cavity axis;
   an elongated member defining an elongated member axis extending axially along the longitudinal cavity axis in the elongated interior cavity, the elongated interior cavity having a diameter that is substantially larger than a diameter of the elongated member;
   an actuator configured to operably engage the elongated member such that as the actuator moves from a first position to a second position, the elongated member is shifted radially within the substantially larger diameter of the elongated interior cavity; and
   a broach configured to engage the elongated member, wherein the elongated member locks the broach to the second orthopedic keel punch impactor portion when the actuator is in the first position.

2. The orthopedic keel punch impactor of claim 1 further comprising a coupling portion provided at a distal end of the elongated member.

3. The orthopedic keel punch impactor of claim 2 further comprising a boss positioned on the second orthopedic keel punch impactor portion at a distal end of the elongated interior cavity, the boss defining a footprint, wherein the coupling portion is substantially contained within the footprint when the actuator is in the second position and a portion of the coupling portion protrudes outside the footprint when the actuator is in the first position.

4. The orthopedic keel punch impactor of claim 2, wherein the coupling portion comprises:
   a flange portion, the flange portion moveable between a third position and a fourth position as the elongated member is shifted laterally within the elongated interior cavity, wherein the flange portion is substantially contained within a footprint of an end portion of the second orthopedic keel punch impactor portion in the second position and protrudes outside the footprint of the end portion in the first position.

5. The orthopedic keel punch impactor of claim 4 wherein a shoulder is formed in a mouth of the broach, and wherein the flange engages the shoulder when the flange is in the first position in order to lock the broach to the second orthopedic keel punch impactor portion.

6. The orthopedic keel punch impactor of claim 1 further comprising a transverse passage provided in the second orthopedic keel punch impactor portion, the transverse passage extending between an outer surface of the second orthopedic keel punch impactor portion and the elongated interior cavity.

7. The orthopedic keel punch impactor of claim 6 wherein the actuator comprises a button positioned in the transverse passage of the second orthopedic keel punch impactor portion.

8. The orthopedic keel punch impactor of claim 7 wherein the button extends from a side of the second orthopedic keel punch impactor portion.

9. The orthopedic keel punch impactor of claim 8 wherein the actuator further comprises a spring configured to bias the button toward the first position.

10. The orthopedic keel punch impactor of claim 1 wherein the elongated member axis shifts from a first axial position to a second axial position that is parallel with the first axial position when the actuator is moved from the first position to the second position.

11. The orthopedic keel punch impactor of claim 1 wherein the first orthopedic keel punch impactor portion further comprises a handle portion.

12. An orthopedic keel punch impactor comprising:
a first orthopedic keel punch impactor portion including an impact surface;
a second orthopedic keel punch impactor portion connected to the first orthopedic keel punch impactor portion, the second orthopedic keel punch impactor portion defining an elongated interior cavity defining a longitudinal cavity axis;
an elongated member defining an elongated member axis extending axially along the longitudinal cavity axis in the elongated interior cavity, the elongated interior cavity having a diameter that is substantially larger than a diameter of the elongated member;
an actuator configured to operably engage the elongated member such that as the actuator moves from a first position to a second position, the elongated member is shifted radially within the substantially larger diameter of the elongated interior cavity;
a coupling portion provided at a distal end of the elongated member;
a boss positioned on the second orthopedic keel punch impactor portion at a distal end of the elongated interior cavity, the boss defining a footprint, wherein the coupling portion is substantially contained within the footprint when the actuator is in the second position and a portion of the coupling portion protrudes outside the footprint when the actuator is in the first position; and
a broach configured to engage the boss at the end of the second orthopedic keel punch impactor portion, the broach including a shoulder, wherein the coupling portion of the elongated member engages the shoulder to lock the broach to the second orthopedic keel punch impactor portion when the actuator is in the first position.

13. The orthopedic keel punch impactor of claim 12, further comprising:
a transverse passage provided in the second orthopedic keel punch impactor portion, the transverse passage extending between an outer surface of the second orthopedic keel punch impactor portion and the elongated interior cavity, wherein the actuator comprises a button positioned in the transverse passage of the second orthopedic keel punch impactor portion.

14. The orthopedic keel punch impactor of claim 13 wherein the actuator further comprises a spring configured to bias the button toward the first position.

15. The orthopedic keel punch impactor of claim 13 wherein the actuator further comprises a spring configured to bias the button toward the first position.

16. An orthopedic keel punch impactor comprising:
a first orthopedic keel punch impactor portion including an impact surface;
a second orthopedic keel punch impactor portion connected to the first orthopedic keel punch impactor portion, the second orthopedic keel punch impactor portion defining an elongated interior cavity defining a longitudinal cavity axis;
an elongated member defining an elongated member axis extending axially along the longitudinal cavity axis in the elongated interior cavity, the elongated interior cavity having a diameter that is substantially larger than a diameter of the elongated member;
an actuator configured to operably engage the elongated member such that as the actuator moves from a first position to a second position, the elongated member is shifted radially within the substantially larger diameter of the elongated interior cavity;
a coupling portion provided at a distal end of the elongated member;
a flange portion, the flange portion moveable between a third position and a fourth position as the elongated member is shifted laterally within the elongated interior cavity, wherein the flange portion is substantially contained within a footprint of an end portion of the second orthopedic keel punch impactor portion in the second position and protrudes outside the footprint of the end portion in the first position; and
a broach, the broach including a mouth configured to receive a distal end portion of the second orthopedic keel punch impactor portion.

17. The orthopedic keel punch impactor of claim 16 wherein a shoulder is formed in the mouth of the broach, and wherein the flange engages the shoulder when the flange is in the first position in order to lock the broach to the second orthopedic keel punch impactor portion.

18. The orthopedic keel punch impactor of claim 16, further comprising:
a transverse passage provided in the second orthopedic keel punch impactor portion, the transverse passage extending between an outer surface of the second orthopedic keel punch impactor portion and the elongated interior cavity, wherein the actuator comprises a button positioned in the transverse passage of the second orthopedic keel punch impactor portion.

* * * * *